United States Patent [19]
Bogert et al.

[11] Patent Number: 5,800,399
[45] Date of Patent: Sep. 1, 1998

[54] LOW-COST METHOD OF ASSEMBLING AN EXTRUDED CANNULA HOLDER FOR A CATHETER INSERTION DEVICE

[75] Inventors: David L. Bogert, Plainville; Zino Altman, Unionville; Thomas Koehler, Simsbury, all of Conn.

[73] Assignee: Johnson & Johnson Medical, Inc., Arlington, Tex.

[21] Appl. No.: 703,706

[22] Filed: Aug. 27, 1996

[51] Int. Cl.⁶ .................................... A61M 5/178
[52] U.S. Cl. .................................... 604/165
[58] Field of Search .................... 604/164, 165, 604/167, 168, 256, 264, 280, 283

[56] References Cited

U.S. PATENT DOCUMENTS

| | | | |
|---|---|---|---|
| 4,046,144 | 9/1977 | McFarlane | 604/168 |
| 4,193,399 | 3/1980 | Robinson | 604/168 |
| 4,193,400 | 3/1980 | Loveless et al. | 604/168 |
| 4,655,750 | 4/1987 | Vaillancourt | 604/165 |
| 4,904,240 | 2/1990 | Hoover | 604/53 |
| 5,013,304 | 5/1991 | Russell et al. | 604/167 |
| 5,053,014 | 10/1991 | Van Heughten | 604/167 |
| 5,066,284 | 11/1991 | Mersch et al. | 604/168 |
| 5,181,523 | 1/1993 | Wendelborn | 604/168 X |
| 5,234,410 | 8/1993 | Graham et al. | 604/167 |
| 5,250,033 | 10/1993 | Evans et al. | 604/167 X |
| 5,575,777 | 11/1996 | Cover et al. | 604/168 X |

*Primary Examiner*—Manuel Mendez
*Attorney, Agent, or Firm*—Joseph F. Shirtz

[57] ABSTRACT

Intravenous catheter insertion devices produced by a low cost method of assembling a catheter structure and cannula holder body. Also disclosed is an extruded cannula and blood chamber securement structure. Moreover, there is also provided a novel structure for the realization of simplified extruded catheter insertion devices in which an extruded plastic element is connected with a steel cannula for attachment to a blood chamber or housing to enable a low cost construction rendering the catheter insertion device simple and inexpensive in assembly and construction for economically disposable single usage thereof.

40 Claims, 5 Drawing Sheets

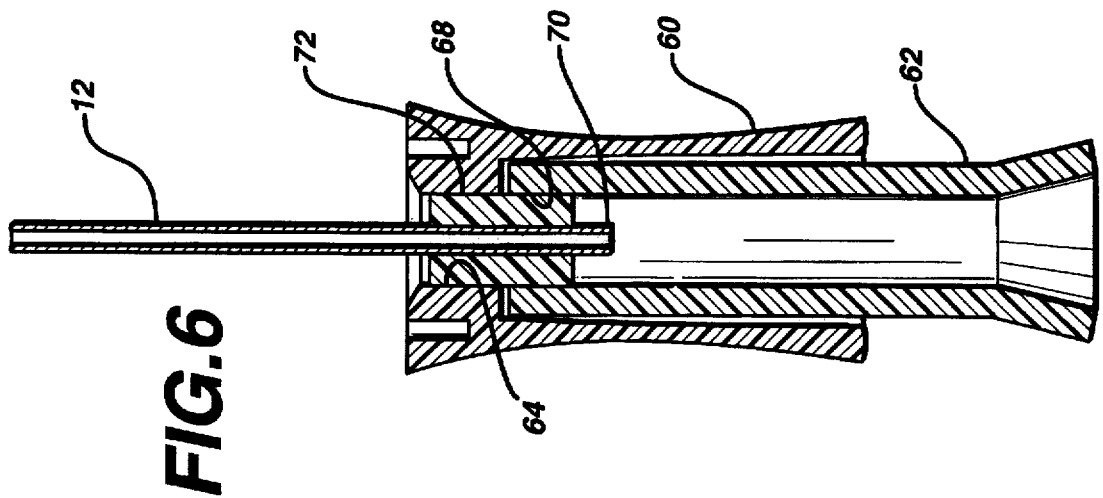
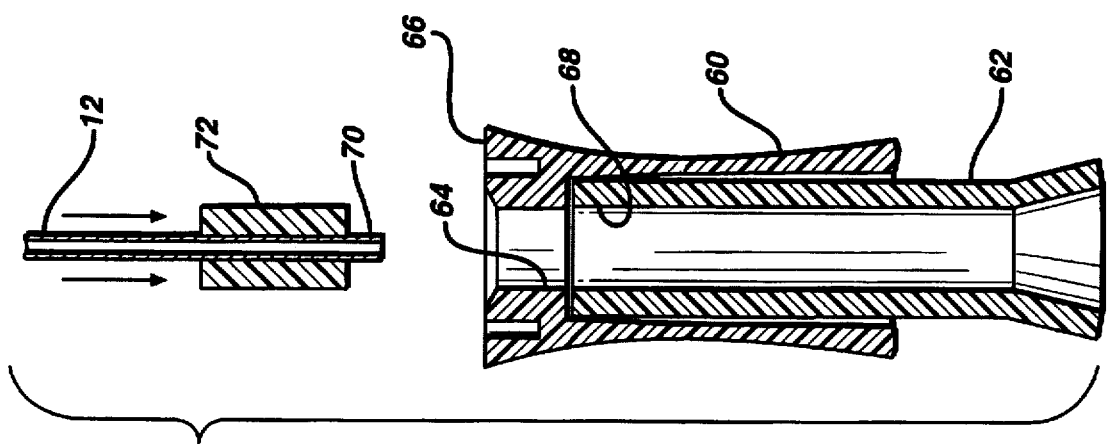

FIG. 9
FIG. 10
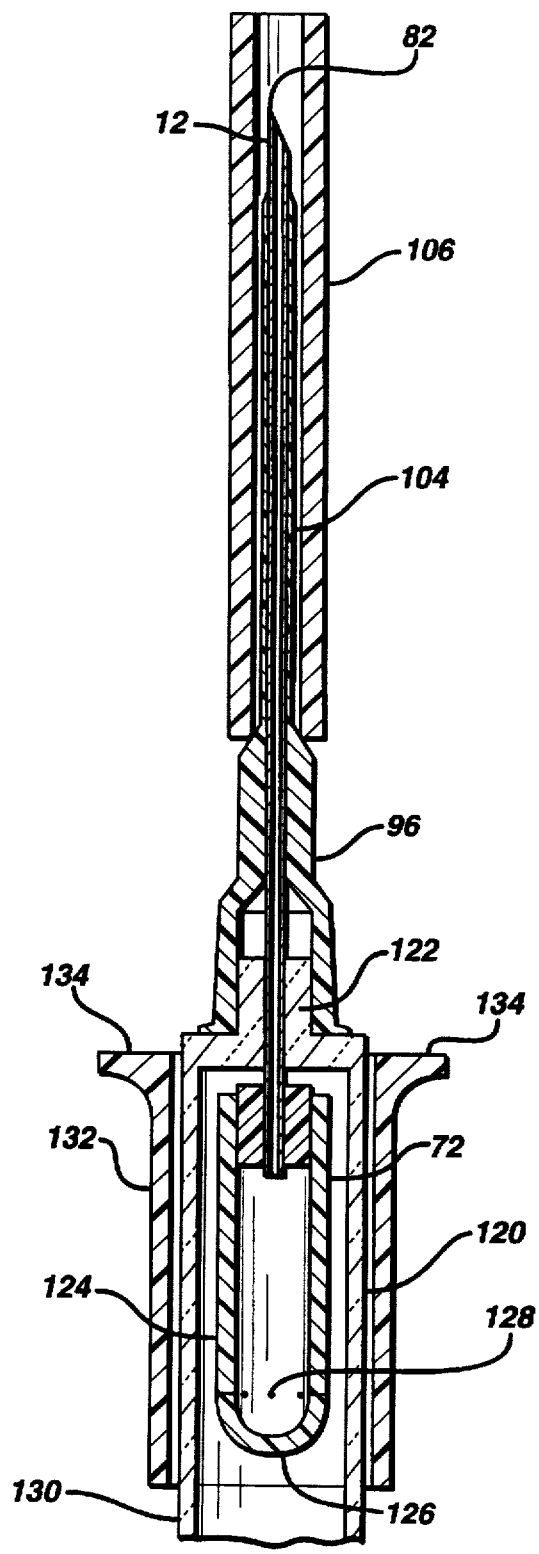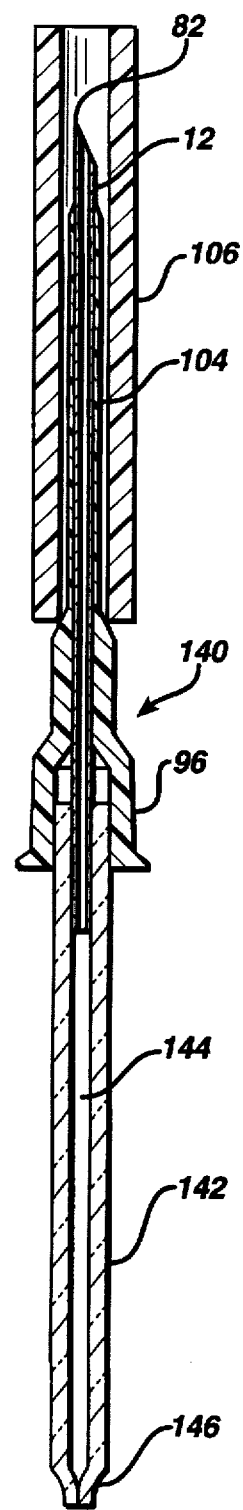

5,800,399

LOW-COST METHOD OF ASSEMBLING AN EXTRUDED CANNULA HOLDER FOR A CATHETER INSERTION DEVICE

BACKGROUND OF THE INVENTION

1. Field of the Invention

The present invention relates, in general, to intravenous catheter insertion devices, and more particularly pertains to a low cost method of assembling a catheter structure and cannula holder body and also relates more specifically to an extruded cannula and blood chamber securement structure. Moreover, the invention is also directed to the provision of a novel structure for the realization of simplified extruded catheter insertion devices in which an extruded plastic element is connected with a steel cannula for attachment to a blood chamber or housing to enable a low cost construction rendering the catheter insertion device simple and inexpensive in assembly and construction for economically disposable single usage thereof.

The utilization of clinical apparatus in which pointed hollow needles or cannulae are employed in order to puncture the skin of a patient, and especially catheters utilizing such needles to effectuate venipunctures, is well known n the medical art and is widely practiced by physicians and clinical personnel for the purpose of injecting fluids and drugs directly into the bloodstream of patients. Additionally, during surgical operations or procedures it may be frequently required that whole blood transfusions and parenteral fluids be administered to a patient undergoing such surgical procedures. Basically, as is well known and has been employed for a considerable length of time, the introduction of such fluids into the cardiovascular systems of patients has necessitated the forming of a venipuncture utilizing a hollow rigid needle having a proximal attachment site for a fluid connection which is adapted to interconnect the needle with a source of intravenously administered fluids.

The foregoing method of administering fluids to patients through venipunctures has been subject to some rather serious problems in the administration of fluids to patients in this medical technology. Thus, a primary concern which had to be addressed resided in the inherent rigidity of the needle, the latter of which is normally generally constituted of surgical-quality steel, and while inserted into the vein of a patient, necessitated the needle to be maintained for reasons of safety in a fixed position at the general site of the venipuncture throughout the duration of fluid administration or transfusion, whereby such a procedure could conceivably consume a considerable length of time. In addition to the foregoing, at times it has been necessary to periodically draw blood samples and/or successively administer intravenous fluids to a patient, thus requiring the patient to be subjected to a series or plurality of venipunctures, each administered at a specific time and at different sites on the body, resulting in a relatively traumatic experience to the patient in view of such repeated and somewhat painful and unpleasant venipunctures.

In order to ameliorate or possibly even eliminate the foregoing problems, in the medical technology it has been more recently the practice to introduce a flexible tubular catheter of a low-friction material, such as a silastic or Teflon into the vein of a patient and to permit the catheter tube to remain in such a position over lengthier periods of time for purposes of; for example, periodically administering fluids, including parenteral fluids, blood/plasma transfusions, medications in liquid form and also for the collection of blood samples and the like. In this manner, the previously encountered trauma, extravasation, and infiltration caused by repeated venipunctures have been largely avoided, and the danger and discomfort to a patient of leaving a rigid needle in the body for a prolonged period of time has been generally overcome. Thus, in order to position the distal end of such a flexible catheter tube within the body cavity of a patient, such as a vascular cavity or vein, there is normally employed a cannula or hollow sharp-tipped needle for the purpose of forming the venipuncture. Thereafter, the flexible catheter tube, which is telescopically and slidably coaxially mounted on the outer circumference of the cannula or hollow needle so as to extend sleeve-like thereabout is advanced along the length of the needle into the vein subsequent to the needle having formed the venipuncture. Thereafter, the needle is adapted to be withdrawn from the interior of the catheter tube, while permitting the latter to remain within the body of the patient at the site of the venipuncture, and the needle is suitably discarded.

Inasmuch as the needle which has been previously positioned in the body of the patient upon forming the venipuncture may have been exposed to infectious agents; for instance, such as a patient infected with the Acquired Immune Deficiency Syndrome (AIDS) which is frequently or practically always ultimately fatal in nature, or other dangerous infectious conditions such as hepatitis, there is present the danger or hazard that the clinical personnel may inadvertently or accidentally jab or stick themselves with the used needle after withdrawal from the body of the patient, with the possibility of infection or even death resulting therefrom. Consequently, upon withdrawal of the needle from the body of the patient, the needle is generally retracted into a protective environment, such as a needle tip protective housing or structure, and safely disposed in conjunction therewith.

2. Discussion of the Prior Art

It is currently the common practice of many developing or undeveloped countries, ordinarily referred to as "third world countries" to reuse a cannula/catheter, such as a steel stylet, many times over in order to reduce medical expenditures. The health hazards which are associated therewith, as mentioned hereinbefore, are quite considerable, not to mention the discomfort to the patients. In order to address this widespread medical problem, it is extremely desirable to be able to provide for an extremely simple, low cost disposable catheter delivery system. At this time, pursuant to the current state of the art catheter delivery systems, the latter generally comprises a sharp steel cannula or stylet which is adhesively bonded within an injection molded body which includes an integral blood chamber which is normally sealed with a porous plug. The difficulties in providing a steel cannula in conjunction with a molded plastic body or blood chamber obviates the drawbacks encountered in molding a plastic body about the steel cannula, inasmuch as difficulties are present in maintaining trueness of the cannula runout, particularly in smaller gauge sizes since it is extremely difficult to accurately maintain a thin steel cannula within a mold when the plastic flow into the mold is rated by thousands of psi. Consequently, the construction of molded body, such as a blood chamber with a steel cannula inserted therein during the molding process is relatively complex and does not always lead to the desired results, thereby causing the entire manufacturing process to become relatively expensive and difficult to market in underdeveloped or developing countries were cost factor is of prime significance, especially with the ordinarily large populations involved, wherein it is almost an absolute necessity for being able to provide a low cost, mass-produced catheter insertion device which is readily and inexpensively disposable.

SUMMARY OF THE INVENTION

According to a particular feature of the invention, there is utilized the concept of employing either a molded element or extruded plastic plug of basically an essentially cylindrical nature which is adapted to maintain the steel cannula in precise runout within the housing, the latter of which may be a blood chamber. To that effect, the housing may be either an extruded or molded element which enables the plug mounting the cannula to be pressed or fitted into place without the requirement for an adhesive or for a corrective runout operation to facilitate appropriate alignment of the cannula relative to the blood chamber and/or the remaining catheter device. This particular construction eases the molding of the blood chamber and facilitates the provision of an extremely narrow and extended blood chamber within the housing, providing a streamlined assembly inasmuch as the blood chamber is not held in the housing at its outside diameter but rather on its inside diameter.

Pursuant to another aspect of the invention, rather than positioning steel cannula by being adhesively bonded within an injection-molded housing body having an integral blood chamber sealed with a porous plug, the invention contemplates constructing the housing body from chopped or cut segments of extruded plastic materials, which are not only easy and inexpensive to produce, but are also extremely simple and readily supplied and assembled in inexpensive automatic equipment which is well suited to the limited economic assets of developing and undeveloped countries. Currently, the catheter insertion systems primarily employ molded parts for the body which retains the steel cannula and forms the blood chamber. In contrast with the foregoing, pursuant to an embodiment of the invention, "chopped" or segmented lengths of extrusion form the body which holds the cannula, whereby one of the extrusion segments acts as a combination finger hold and blood chamber, and the other extrusion acts as a combination nose portion and cannula holder. This embodiment utilizes a porous plug to vent the blood chamber and an end distant from its retention of the cannula.

In accordance with a modification, one extrusion may be readily employed to hold the cannula in place in a molded part, whereas the venting for the blood chamber is formed by means of a laser. A further modification relates to a safety catheter system whereby the extrusion holds one cannula end portion within a molded housing or blood chamber, and the venting for the blood chamber is formed through either a laser or a porous plug.

Another embodiment utilizes a single extrusion to perform the multiple duties of holding the cannula, providing the finger hold and the blood chamber, and also provides the vent for the blood chamber. This embodiment is considered to be essentially the ultimate in simplicity and low cost, both as to construction and high volume manufacturing or mass-production technology required so as to enable it to be designed as a catheter insertion device which is economically disposable after only a single use, and is particularly suitable for undeveloped or developing countries having large and dense populations where cost factor is the primary consideration.

In all of the foregoing embodiments, the steel cannula is pressed into position without the use of adhesives, while the catheter of the insertion device preferably would be constituted of a unitary component, molded either through thermally cycled molding or through stretch molding. Moreover, a protective sheath for this catheter insertion device would be another simple length of a chopped extrusion which is adapted to be fitted over the tip of the catheter hub rather than fitted to the housing body or blood chamber.

The inventive embodiments are all designed to provide simpler and less expensive methods of forming catheter insertion devices and the structures derived from such methods which render economically viable the discarding of the devices after only a single use, thereby considerably reducing the hazards of infection encountered by patients treated with reused catheter insertion devices, while also protecting medical and clinical personnel.

Accordingly, it is an object of the present invention to provide a novel and simply constructed catheter insertion device wherein an extruded plastic plug is adapted to maintain a cannula in a housing, the latter of which may be a blood chamber.

Another object of the present invention is to provide a simply constructed catheter insertion device wherein the interconnection between a cannula and a housing is rendered simple in its construction and facilitates production methods rendering the entire device economically viable for discarding thereof after only a single use.

BRIEF DESCRIPTION OF THE DRAWINGS

Reference may now be had to the following detailed description of preferred embodiments of the invention, taken in conjunction with the accompanying drawings; in which:

FIG. 5 illustrates an exploded longitudinal sectional view of an extruded segment forming a gasket for a cannula of a blood chamber securement in the process of being assembled;

FIG. 6 illustrates the and blood chamber securement of FIG. 5, shown in the assembled condition thereof;

FIG. 9 illustrates a further embodiment of an extruded catheter insertion device similar to that shown in FIG. 7; and FIG. 10 illustrates still another embodiment of an extruded catheter insertion device similar to FIG. 7.

DETAILED DESCRIPTION OF PREFERRED EMBODIMENTS

Figure 1:
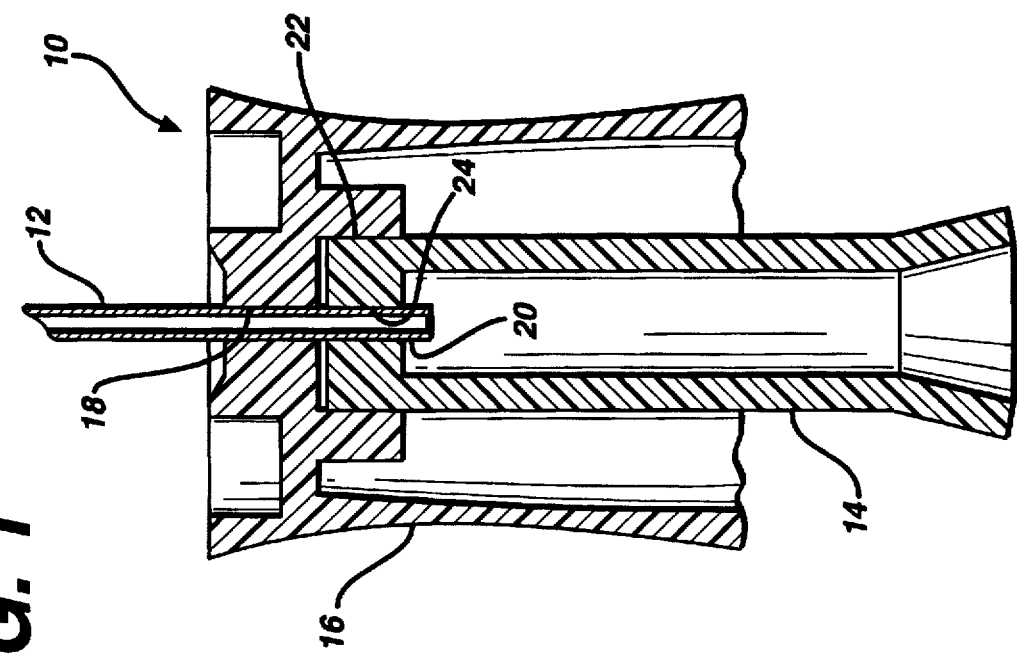

Referring now in specific detail to the drawing of FIG. 1, there is shown a construction of an arrangement 10 for retaining a steel cannula 12 in a molded component 14; for example, such as a blood chamber, as currently employed in the technology.

Throughout the various hereinbelow described embodiments, identical or similar components are identified by the same reference numerals.

In this instance, a molded plastic finger holder 16 has a central aperture 18 retaining the steel cannula or stylet 12 in a close fitting relationship. The end 20 of the cannula 12 which extends axially inwardly into the finger holder 16, is fixedly connected with an end 22 of the molded housing 14, which may be a blood chamber, and is molded therewith during the molding operation forming the housing or component 14 by being fitted to extend through bore 24. In that instance, it is rather difficult to maintain the cannula runout or its positioning, particularly in the smaller gauge sizes. The reason for the foregoing resides in that it is extremely difficult to maintain a small or thin steel pin, such as cannula 12 in a mold while the plastic for producing component 14 flows into the mold and is rated by thousands of psi. Consequently, the process in forming the composite molded plastic component and steel cannula through a molding operation frequently leads to a large number of rejects, which not only renders the process complex and expensive but also causes the large number of rejects to further increase the cost per unit in manufacturing the cannula and blood chamber securement for a catheter insertion device.

Figure 2:
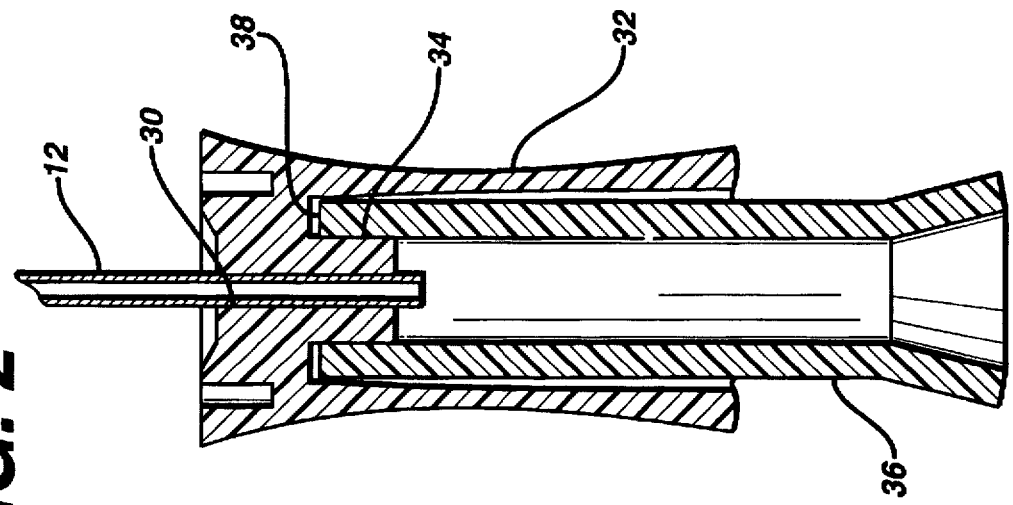
FIGS. 1 through 4 illustrate various embodiments for supporting cannulae in molded components forming part of a catheter insertion device, pursuant to the current state of the art.

Reverting to FIG. 2, in that instance, the steel cannula 12 is fixedly molded in a bore 30 of the finger holder 32, with the latter clampingly engaging in an annular recess 34 the molded blood chamber or housing 36 at one end 38 thereof. As in the embodiment of FIG. 1, in this case, the runout of the steel cannula 12 is also difficult to maintain, leading to a large number of rejects during the manufacture of the catheter insertion device.

Figure 3:
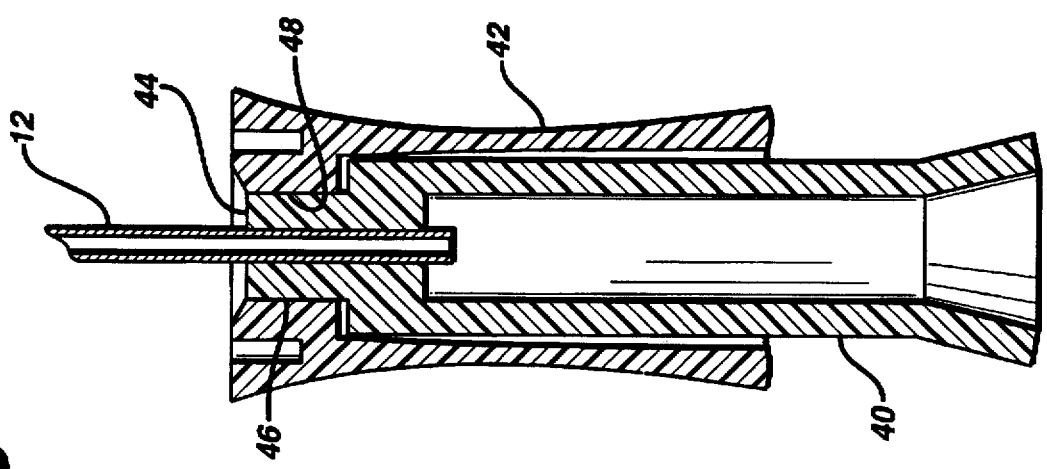

Regarding the embodiment of FIG. 3 of the drawings, in that instance, the cannula 12 rather than being molded into the blood chamber or housing 40 and also into the finger holder 42 as in FIG. 1, or in the finger holder 32 per se as shown in FIG. 2; in this instance the cannula 12 is molded into a forwardly extending hub portion 44 at the end 46 of the blood chamber or housing 40, the latter of which is then clampingly fitted into a central aperture or bore 48 formed in the finger holder 42. This again leads to potential difficulties in maintaining the runout of the cannula in its appropriate orientation or required degree of trueness.

Figure 4:
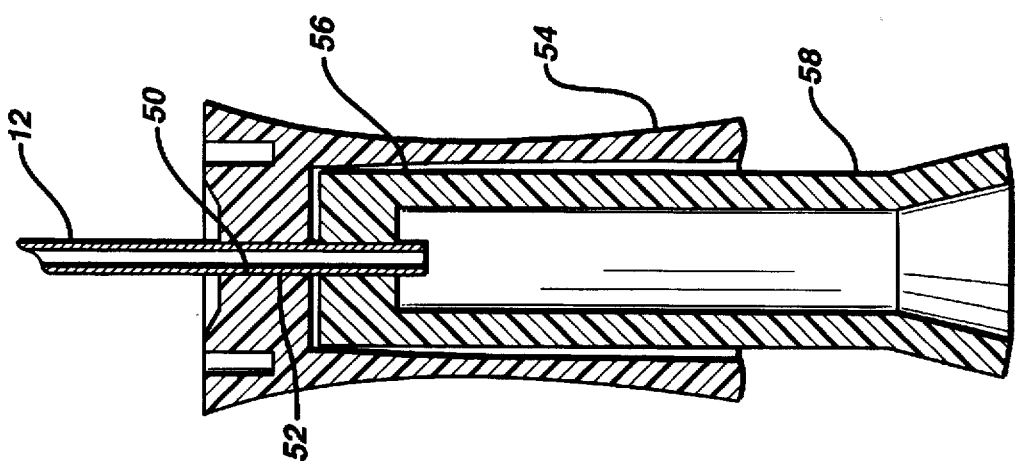

Concerning the embodiment of FIG. 4 of the drawings, in that instance, the cannula 12 is again molded into a bore 50 centrally extending through an end 52 of the finger holder 54 and through the end portion 56 of the blood chamber or housing 58, and wherein the blood chamber is loosely positioned within the finger holder, requiring the steel cannula 12 to maintain its axially oriented integrity relative to the blood chamber 58 and the finger holder 54. This again will adversely affect the trueness of the cannula runout, and render the entire arrangement difficult to manufacture in view of the precision required in the molding of the components and the maintaining of the cannula 12 in its correct or true runout position.

In order to provide a simple construction for the blood chamber securement structure of the catheter insertion device, which is inexpensive while rendering the runout of the cannula 12 precise and true relative to the extent of the finger holder 60 and the blood chamber 62, as shown in FIG. 5 of the drawings, the finger holder 60 which may be a molded plastic component has a central bore 64 in an end 66 thereof which is in alignment with a central bore 68 in the blood chamber 62, the latter of which may be either of a molded or extruded plastic material construction. The cannula 12, which is a rigid steel stylet having a sharp insertion point (not shown) for forming a venipuncture in a patient, has the opposite or rearward end 70 thereof encompassed by a gasket 72 in a closely fitted or interference fit, the gasket being in the shape of an extruded cylindrical segment or so-called "plug". The gasket 72 may be constituted of extruded urethane, PEBAX, crosslinked polyolefin which may be filled with mica, DE, silica gel, and the like, among other suitable plastic materials, and does not require any adhesive to be interposed between the gasket 72 and the cannula 12.

As illustrated in FIG. 6, wherein the blood chamber securement components are shown in their assembled position, the gasket 72 in conjunction with the cannula 12 fixed therein is press-fitted into the aligned bores 64 and 68 of the finger holder 60 and the blood chamber 62; for example, at an 0.001 to 0.020 mm interference with both bores in the finger holder and blood chamber, thereby clampingly interengaging all of the components while maintaining the trueness or correctness of the runout of the cannula 12 in a simple manner.

The foregoing arrangement may have the finger holder 60 constituted from a suitable molded rigid plastic material which is lubricious, such as an opaque nylon, polyester or polyolefin; whereas the blood chamber 62 may be either a molded element or extruded from a tubular member and formed of clear ABS, polypropylene, modified acrylic or other similar type of material. This blood chamber securement assembly does not require any adhesive or ultraviolet curing of the material, and does not necessitate the use of complex molded parts; with the process including only a single assembly step and only two gauge-specific components consisting of the gasket 72 and the cannula 12. Moreover, the blood chamber 62 is maintained in its correct position relative to the finger holder 60 by the plug or gasket 72 rather than having to correlate its external diameter with an internal cylindrical surface on the finger holder 60, thereby further rendering the manufacturing process simpler and less expensive when compared with the current state-of-the-art, as represented by the embodiments of FIGS. 1 through 4 of the drawings.

Figure 7:
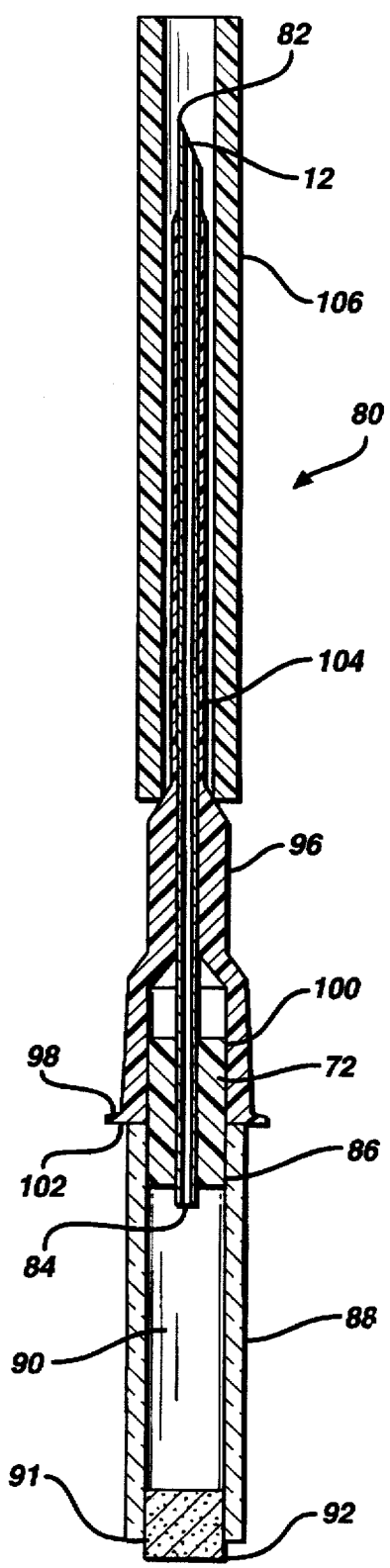
FIG. 7 illustrates a longitudinal sectional view of an embodiment of an extruded catheter insertion device pursuant to the invention.

Reverting to the extruded catheter insertion device 80 illustrated in FIG. 7 of the drawings, there is illustrated a steel cannula 12 having a sharp venipuncture-forming insertion point 82, the opposite end 84 of the cannula 12 being press-fitted into an extruded cannula holder in the shape of a hollow plug or tubular segment forming a gasket 72 similar to that as shown and described in FIGS. 5 and 6. In this embodiment, press-fitted onto the rearward portion 86 about the periphery of the extruded cannula holding gasket 72 is an extruded plastic member, such as a hollow cylindrical member or tubular body 88 which is adapted to form a blood chamber 90, the distal end 91 of which is adapted to be sealed by a porous solid plug 92 to facilitate venting of any blood contents received therein.

A catheter 96 consisting of a single piece, which may be either of a stretch molded or thermally cycle molded plastic material, includes a finger holding flanged hub 98 which extends in closely fitted relationship about the forward portion 100 of the extruded cannula retaining gasket 72, with the bottom surface 102 of hub 98 contacting the end of cylindrical member 88. An elongate tubular portion 104 of the catheter 96 extends from hub 98 in close fit about the exterior surface of the steel cannula 12 toward the tip or point 82. The portion of the steel cannula 12 having the catheter portion 104 thereon may be protectively encompassed by a removable extruded plastic tubular sheath 106. In this embodiment, the various components may be rapidly and inexpensively produced through the formation of primarily simple and extruded tubular components of plastic material, most of which are not required to be designed to very close tolerances, and consequently can be supplied to and assembled in simple and inexpensive apparatus. Moreover eliminated are ultrasonics, adhesives, ultraviolet ovens, and other complex processes and/or installations, all of which renders the present catheter insertion design simple and inexpensive for worldwide and universal production and use, particularly such as in developing or undeveloped countries so as to adapt these devices to be economically disposable after only a single use.

Figure 8:
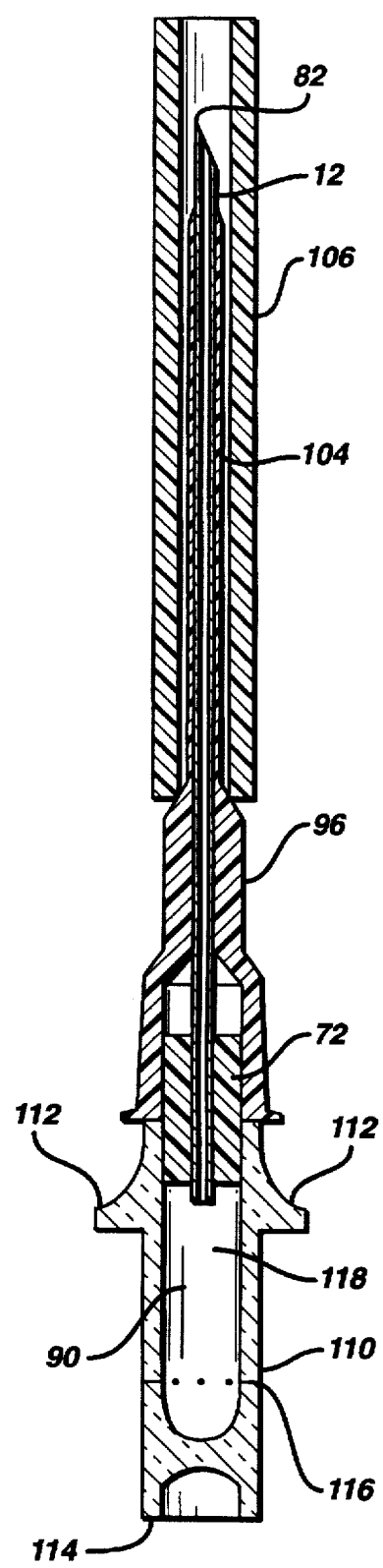
FIG. 8 illustrates a view similar to FIG. 7 of a modified embodiment of the extruded catheter insertion device.

With regard to the embodiment of FIG. 8 of the drawings, wherein elements which are similar to or identical with those in FIG. 7, are identified by the same reference numerals, in this instance the primary distinction resides in that rather than employing an extruded blood chamber body of tubular construction and a solid plug for venting the blood chamber, there is provided a molded plastic blood chamber body 110 having integral external finger holds 112 formed thereon, and in which the distal end 114 of the molded blood chamber body 110 is closed off rather than having an opening including a porous venting plug. In this embodiment, laser-cut vents 116 may be provided for the blood supply which is drawn into the blood chamber 118, or alternatively, as in the embodiment of FIG. 7, a porous venting plug 92 may be employed with the molded blood chamber body 110 incorporating the integrally molded finger holds 112. Herein, although the blood chamber body 110 is of a more complex molded nature than the extruded body element 88 of FIG. 7, it is simply constructed with integral molded finger holds, thereby also rendering feasible a process of producing a low cost catheter with integral finger holding structure.

In the embodiment of FIG. 9 of the drawings, in which elements which are similar to or identical with those of the embodiments of FIGS. 7 and 8 are identified by the same reference numerals, there is formed a cylindrical nose guard 120 having a projecting hub 122 extending sealingly about the cannula 12, and with the cannula holder consisting of an extruded gasket 72 having either an extruded or molded tubular blood chamber 124 attached thereto by means of an interference fit. The opposite or distal end 126 of the blood chamber 124 may be of closed construction and provided with laser vents 128 for blood drawn into the blood chamber, or alternatively, as in FIG. 7 of the drawings, provided with a porous venting plug 92 permitting venting of the contents of the blood chamber.

The circumference of the blood chamber 124 is encompassed in spaced relationship by a cylindrical wall portion 130 of the nose guard 120, and in turn, the latter is encompassed by a molded body or housing 132 with integral finger holds 134, thereby providing a blood chamber securement portion for the catheter insertion device. As in the previous embodiments, a removable extruded cylindrical or tubular plastic sheath 106 may encompass the catheter and steel cannula so as to protect a user from needle stick by the sharp point 82 of the cannula 12.

Pertaining to the embodiment of FIG. 10 of the drawings, in which elements similar to or identical with those shown in FIGS. 7 to 9 are identified by the same reference numerals, in this instance, the blood chamber securement structure is further simplified in that, rather than utilizing an extruded plug having the rearward end of the cannula 12 press-fitted therein, an extruded unitary cannula holder, finger holder and blood chamber 140 consisting of a hollow tubular member 142 forms the blood chamber 144, and with the distal end 146 being crimped closed to form a partial vent for blood withdrawn into the blood chamber 144 upon use of the catheter insertion device. For the remainder, the catheter and the extruded tubular sheath for protecting the cannula is identical with the embodiments of FIGS. 7 to 9. However, in this embodiment, due to the extremely simple design thereof which is primarily constituted of "chopped" or tubular segments of extrusions, and with the only molded element being the one-piece catheter, there is provided an extremely low cost catheter insertion device for applications in which cost is the overriding factor, and the potential of blood leakage and contact is not particularly important or significant. This particular catheter insertion device is especially suitable for widespread utilization in developing or undeveloped countries wherein it is a prime necessity to be able to provide disposable catheter insertion devices at extremely low cost and with simplicity in manufacturer and use.

From the foregoing it becomes readily apparent that the invention is directed to extremely simple methods of providing extruded catheter insertion devices and blood chamber securements which are extremely cost effective and are adapted for single use and disposal especially suited for developing or undeveloped so called "third world" countries.

While there has been shown and described what are considered to be preferred embodiments of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. A method of producing a securement between a cannula and a chamber structure for a catheter insertion device; said method comprising:

(a) arranging an elongated cannula in fixed sealed position to extend through an axial central through-bore in an extruded plastic cylindrical member, a major length of said cannula projecting from a first end of said cylindrical member and terminating in a sharp point to facilitate insertion thereof into the body of a patient, and a shorter length of said cannula protruding from a second end of said cylindrical member;

(b) and a chamber structure having an end defining an opening having a diameter in close conformance with an outer diameter of said cylindrical member being fastened to said cylindrical member by extending at least a portion of an axial length of said cylindrical member into said chamber structure in press-fitted sealing engagement therewith.

2. A method as claimed in claim 1, wherein the outer diameter of said cylindrical member and the diameter of the opening in said chamber structure are dimensioned to provide an interference fit forming said sealing engagement.

3. A method as claimed in claim 2, wherein the interference fit between the outer diameter of the cylindrical member and the diameter of the opening in said chamber structure is in a magnitude of about 0.001 to 0.020 inches.

4. A method as claimed in claim 1, wherein said extruded cylindrical member is cut to length from a continuously extruded tubular extrudate.

5. A method as claimed in claim 1, wherein said chamber structure is formed from an elongated extruded plastic hollow cylindrical body.

6. A method as claimed in claim 1, wherein said chamber structure is formed from an elongated molded plastic hollow cylindrical body.

7. A method as claimed in claim 1, wherein a plastic finger hold for said catheter insertion device is constituted of a cylindrical element, said finger hold being positioned on the end of said chamber structure possessing said opening and including a cylindrical wall portion encompassing at least a portion of the axial length of said chamber structure.

8. A method as claimed in claim 7, wherein the portion of the finger hold which is positioned at the end of said chamber structure includes a through aperture dimensioned in conformance with the size of the opening in said chamber structure, said extruded cylindrical member being press-fitted through said aperture so as to sealingly engage the through-aperture of said finger hold.

9. A method as claimed in claim 1, wherein a finger hold for said catheter insertion device is integrally molded with said chamber structure.

10. A method as claimed in claim 1, wherein a molded catheter closely encompasses substantially the major portion of the length of said cannula, said catheter having a hub positioned with an interference fit on a portion of the outer surface of said cylindrical member adjoining the portion having the chamber structure in sealing engagement therewith.

11. A method as claimed in claim 1, wherein a nose guard extends about at least a portion of the length of said chamber structure, said nose guard having an end fastened to said cannula, a molded catheter closely encompassing substantially the major portion of the length of said cannula; a hub of said catheter being mounted on a protuberance of said nose guard; and a housing body including integral finger holds encompassing said nose guard and chamber structure.

12. A method as claimed in claim 1, wherein said cylindrical member and said chamber structure are unitarily formed from an extruded plastic member.

13. A method as claimed in claim 1, wherein said chamber structure comprises a blood chamber.

14. A method as claimed in claim 13, wherein a porous plug is inserted into an end of said chamber structure distant from the end having the opening provided therein.

15. A method as claimed in claim 13, wherein laser-cut vent holes are formed in said blood chamber proximate an end thereof which is distant from the end having the opening provided therein.

16. A method as claimed in claim 13, wherein an end of said chamber which is distant from the end provided with the opening therein is crimped to form a partial vent.

17. A method as claimed in claim 1, wherein said extruded cylindrical member forms a gasket of a material selected from the group of materials consisting of extruded urethane, PEBAX, and crosslinked polyolefin which is filled with MICA, DE, or silica gel.

18. A method as claimed in claim 7, wherein said finger hold is molded of a material selected from the group of materials consisting of molded stiff lubricious opaque nylon, polyester and polyolefin.

19. A method as claimed in claim 1, wherein said chamber structure is formed of a material selected from the group of materials consisting of clear ABS, polypropylene and modified acrylic.

20. A method as claimed in claim 10, wherein a removable extruded plastic sheath is protectively positionable so as to extend over said catheter and cannula.

21. An arrangement forming a securement between a cannula and a chamber structure for a catheter insertion device; said arrangement comprising:

(a) an elongated cannula being arranged in fixed sealed position to extend through an axial central through-bore in an extruded plastic cylindrical member, a major length of said cannula projecting from a first end of said cylindrical member and terminating in a sharp point to facilitate insertion thereof into the body of a patient, and a shorter length of said cannula protruding from an opposite end of said cylindrical member;

(b) and a chamber structure having an opening defined at one end thereof of a diameter in close conformance with the outer diameter of said cylindrical member being fastened to said cylindrical member by at least a portion of said cylindrical member extending into said chamber structure in press-fitted sealing engagement therewith.

22. An arrangement as claimed in claim 21, wherein the outer diameter of said cylindrical member and the diameter of the opening in said chamber structure are dimensioned to provide an interference fit forming said sealing engagement.

23. An arrangement as claimed in claim 22, wherein the interference fit between the outer diameter of the cylindrical member and the diameter of the opening in said chamber structure is in a magnitude of about 0.001 to 0.020 inches.

24. An arrangement as claimed in claim 21, wherein said extruded cylindrical member is a segment of a continuously extruded tubular plastic structure.

25. An arrangement as claimed in claim 21, wherein said chamber structure comprises an elongated extruded plastic hollow cylindrical body.

26. An arrangement as claimed in claim 21, wherein said chamber structure comprises an elongated molded plastic hollow cylindrical body.

27. An arrangement as claimed in claim 21, wherein a plastic finger hold for said catheter insertion device comprises a cylindrical element which is positioned on an end of said chamber structure possessing said opening and includes a cylindrical wall portion encompassing at least a portion of the axial length of said chamber structure.

28. An arrangement as claimed in claim 27, wherein the portion of the finger hold which is positioned at the end of said chamber structure includes a through aperture dimensioned in conformance with the size of the opening in said chamber structure, said extruded cylindrical member being press-fitted through said aperture so as to sealingly engage the through-aperture of said finger hold.

29. An arrangement as claimed in claim 21, wherein a finger hold for said catheter insertion device is integrally molded with said chamber structure.

30. An arrangement as claimed in claim 21, wherein a molded catheter closely encompasses substantialy the major portion of the length of said cannula, siad catheter having a hub positioned with an interference fit on a portion of the outer surface of said cylindrical member adjoining the portion having the chamber structure in sealing engagement therewith.

31. An arrangement as claimed in claim 21, wherein a nose guard extends about at least a portion of the length of said chamber structure, said nose guard having an end fastened to said cannula, a molded catheter closely encompassing substantially the major portion of the length of said cannula; a hub of said catheter being mounted on a protuberance of said nose guard; and a housing body including integral finger holds encompassing said nose guard and chamber structure.

32. An arrangement as claimed in claim 21, wherein said cylindrical member and said chamber structure are unitarily formed from an extruded plastic member.

33. An arrangement as claimed in claim 21, wherein said chamber structure comprises a blood chamber.

34. An arrangement as claimed in claim 33, wherein a porous plug positioned in an end of said chamber structure distant from the end having the opening provided therein.

35. An arrangement as claimed in claim 33, wherein laser-cut vent holes are formed in said blood chamber proximate an end thereof which is distant from the end having the opening provided therein.

36. An arrangement as claimed in claim 33, wherein an end of said chamber which is distant from the end provided with the opening therein is crimped to form a partial vent.

37. An arrangement as claimed in claim 21, wherein said extruded cylindrical member form a gasket of a material selected from the group of materials consisting of extruded urethane, PEBAX, and crosslinked polyolefin which is filled with MICA, DE, or silica gel.

38. An arrangement as claimed in claim 27, wherein said finger hold is molded of a material selected from the group of materials consisting of molded stiff lubricious opaque nylon, polyester and polyolefin.

39. An arrangement as claimed in claim 21, wherein said chamber structure is formed of a material selected from the group of materials consisting of clear ABS, polypropylene and modified acrylic.

40. An arrangement as claimed in claim 30, wherein a removable extruded plastic sheath is protectively to extend over said catheter and cannula.

* * * * *